United States Patent
Semaan

(10) Patent No.: US 9,896,859 B2
(45) Date of Patent: Feb. 20, 2018

(54) LINK-PLATE CONNECTION FOR MONOPOLE REINFORCING BARS

(71) Applicant: Robert Semaan, Miami, FL (US)

(72) Inventor: Robert Semaan, Miami, FL (US)

(73) Assignee: TOWER ENGINEERING SOLUTIONS, LLC, Las Vegas, NV (US)

( * ) Notice: Subject to any disclaimer, the term of this patent is extended or adjusted under 35 U.S.C. 154(b) by 0 days.

(21) Appl. No.: 15/371,708

(22) Filed: Dec. 7, 2016

(65) Prior Publication Data

US 2017/0081872 A1 Mar. 23, 2017

Related U.S. Application Data

(62) Division of application No. 14/552,263, filed on Nov. 24, 2014, now Pat. No. 9,546,497.

(60) Provisional application No. 62/026,522, filed on Jul. 18, 2014.

(51) Int. Cl.
| | | |
|---|---|---|
| *E04H 12/00* | (2006.01) | |
| *E04H 12/08* | (2006.01) | |
| *C01B 6/24* | (2006.01) | |
| *C07B 31/00* | (2006.01) | |
| *C07D 295/03* | (2006.01) | |
| *E04C 5/06* | (2006.01) | |
| *E04H 12/22* | (2006.01) | |

(52) U.S. Cl.
CPC .............. *E04H 12/08* (2013.01); *C01B 6/24* (2013.01); *C07B 31/00* (2013.01); *C07D 295/03* (2013.01); *E04C 5/06* (2013.01); *E04H 12/2292* (2013.01)

(58) Field of Classification Search
CPC ................. E04H 12/2292; E04H 12/24; E04C 2003/026; Y10T 403/66; Y10T 403/50
USPC .................................................. 403/DIG. 15
See application file for complete search history.

(56) References Cited

U.S. PATENT DOCUMENTS

| | | |
|---|---|---|
| 278,617 A | 5/1883 | Smith |
| 731,752 A | 6/1903 | Cadwell |
| 1,817,342 A | 8/1931 | Beecher et al. |
| 2,963,127 A | 12/1960 | Manville |
| 3,077,009 A | 2/1963 | Taber et al. |
| 4,024,688 A | 5/1977 | Calini |
| 4,032,244 A | 6/1977 | Quayle |
| 4,092,079 A | 5/1978 | Swanson |
| 4,645,228 A | 2/1987 | Bertonneau |
| 4,854,665 A | 8/1989 | Gagnon |
| 4,987,718 A | 1/1991 | Knight |
| 5,240,032 A | 8/1993 | Mizioch |
| 6,170,218 B1 | 1/2001 | Shahnazarian |
| 7,267,375 B1 | 9/2007 | Sorkin |
| 7,273,238 B1 | 9/2007 | Sorkin |
| 7,849,659 B2 | 12/2010 | Kopshever, Sr. |
| 7,905,069 B1 | 3/2011 | Lockwood |
| 8,657,344 B2 | 2/2014 | Glazik et al. |
| 2003/0012596 A1 | 1/2003 | Copping |
| 2004/0071507 A1 | 4/2004 | Kim |
| 2006/0196878 A1 | 9/2006 | Cook |
| 2006/0228170 A1 | 10/2006 | Joo |
| 2012/0230757 A1 | 9/2012 | Amikura et al. |
| 2012/0263554 A1 | 10/2012 | Sanz Gamboa |

(Continued)

*Primary Examiner* — Gisele Ford
(74) *Attorney, Agent, or Firm* — Baker & Hostetler LLP

(57) ABSTRACT

Reinforcing bars include load transfer connectors. A link plate includes openings that mate with the load transfer connectors to overlie the splice between reinforcing bars being spliced. A cover plate may be fastened over the link plate.

19 Claims, 3 Drawing Sheets

(56) References Cited

U.S. PATENT DOCUMENTS

2014/0053500 A1     2/2014   Lassiter
2014/0083046 A1     3/2014   Yang

US 9,896,859 B2

LINK-PLATE CONNECTION FOR MONOPOLE REINFORCING BARS

CROSS REFERENCE TO RELATED APPLICATIONS

The present application is a divisional of U.S. application Ser. No. 14/552,263 filed Nov. 24, 2014, which claims the priority of U.S. Provisional Application No. 62/026,522, entitled "Link-Plate Boltless Connection For Monopole Flat Plate Reinforcement," filed on Jul. 18, 2014, the disclosures of which are incorporated herein by reference in their entireties.

FIELD OF THE INVENTION

The present application relates to methods and devices for reinforcing monopoles. More specifically, the present invention includes link-plates reinforcing plates/bars attached to monopoles, where the link-plates include holes that mate with blocks welded or loose to pole reinforcing plates to provide a positive connection for transferring the axial loads between the two reinforcing plates/bars.

BACKGROUND OF THE INVENTION

The wireless telecommunications industry has been growing steadily for a number of years. Consumers continue to demand more coverage, faster access and improved functionality of wireless devices. The advent of data (in addition to voice) has taxed the ability of current networks to support the increased traffic and wireless Carriers are deploying newer, larger and more complex antennas and equipment to increase capacity. This affects both new and existing sites.

New sites are designed to support the larger and heavier equipment—but building new sites is very expensive and is usually done as a last resort and only when coverage areas are to be extended. The more common practice is to use existing sites and to simply replace equipment and antennas as needed. However, existing sites were not always designed for the lateral loads caused by the wind forces on the additional equipment and the supporting monopole must be augmented structurally to allow for these larger antennas and equipment.

A common type of tower built in densely populated urban areas is the monopole. These monopoles are usually multi-sided or round tapered or straight tubular structures with a very small profile and hence more attractive from a zoning and siting approval standpoint. However, these are also the more difficult to augment or modify structurally since the bolting of additional structural elements must be done from the outside as they are too narrow to access from the inside.

One of the more common methods of strengthening these monopoles has been the addition of flat plates or bars to the "flats or flat sides" of the multi-sided structures. Similar concepts are used for cylindrical structures. While this is fairly simple using bolts that can be installed from the outside, the magnitude of the forces seen in the flat plates or bars require very large quantities of bolts at the splice connections between the flat plates or bars for load transfer. For example, a typical splice requires the use of eighteen or more splice bolts per splice per reinforcing plate. Thus, a four-sided plate augmentation design would require seventy-two bolts at each splice elevation. Reinforcing a monopole from the ground to a one-hundred twenty foot elevation may require five or more splices, resulting in more than four-hundred bolts and four-hundred bolt holes to be drilled in the air in the field. As may be appreciated, drilling bolt holes into the monopole and installing such flat plates at elevated heights can be very costly and labor intensive.

As wireless networks continue to tax the structural capacity of existing monopole structures, structural augmentation of these structures with flat plate reinforcing solutions will continue.

SUMMARY OF THE INVENTION

Embodiments of the present invention include a device for reinforcing a monopole. In one optional embodiment, a device includes a plurality of reinforcing plates or bars each having ends and a surface. Each of the reinforcing plates or bars includes at least one or two load transfer connectors attached to the reinforcing bar, proximate to at least one of the ends. The load transfer connectors may be attached to the reinforcing bars (such as by welding) or may be integrally formed with the reinforcing bars or keyed in holes in the reinforcing bars. In one optional embodiment, the load transfer connectors are attached to the reinforcing bar surface. In another optional embodiment, the load transfer connectors may fit into openings in the reinforcing bar.

A device also includes a link-plate having one or more openings shaped to mate with the load transfer connectors. In this manner, adjoining reinforcing bars may be spliced by overlaying the link plate over the reinforcing bars and mating the link plate openings with the load transfer connectors (also referred to as shear blocks) of each adjoining reinforcing bar. In an optional embodiment, the mating connection between the link plate openings and the load transfer connectors may be an interference fit, as known as a press fit or a friction fit, as those terms are commonly understood in mechanical engineering.

In an optional embodiment, the device may further include cover plate positioned to overlie the link plate openings while mated with the load transfer connectors.

DESCRIPTION

Figure 1:
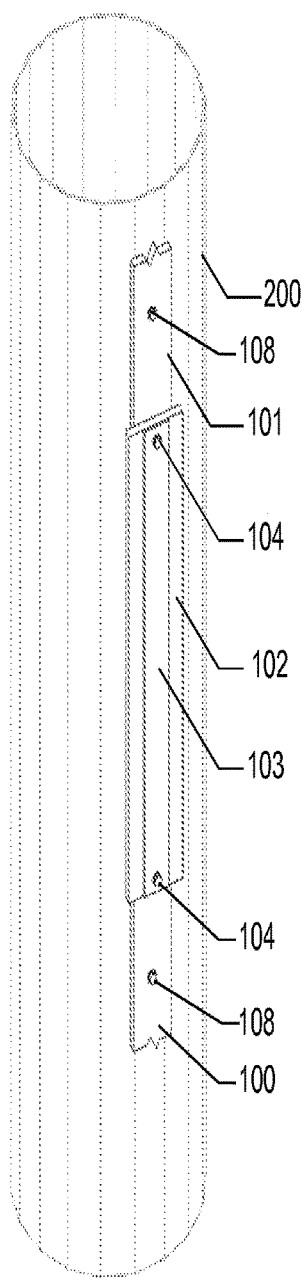
FIG. 1 is an elevated perspective view of a pole and assembled link-plate according to an embodiment of the present invention.

Reference is now made to the figures wherein like parts are referred to by like numerals throughout. The present invention is a system for reinforcing a monopole which includes multiple reinforcing bars 100, 101. In the optional embodiment illustrated in FIGS. 1-8, each reinforcing bar 100, 101 includes an elongated, flat plate section, although the shape and dimensions of the reinforcing bars 100, 101 may vary depending on the optional embodiment. As illustrated in the figures, the plate sections of the reinforcing bars 100, 101 are sized and shaped to lie along the surface of a monopole 200. For example, in an optional embodiment in which the monopole 200 has a polygonal cross-section, the plate section of the reinforcing bars 100, 101 may be flat. In other optional embodiments in which the monopole 200 has a different shape, such as a cylindrical cross-section, the plate section of the reinforcing bars may have a different shape.

The reinforcing bars 100, 101 are secured to the monopole 200, optionally using bolts or other fasteners 108. As explained in greater detail below, the reinforcing bars 100, 101 are linked together to reinforce the monopole, whether the reinforcing bars are subjected to compression or tension forces.

The reinforcing bars 100, 101 also include load transfer connectors 105 (also referred to as "shear blocks"). In the optional embodiments illustrated in FIGS. 1-5, the load transfer connectors are rectangular. However, it is contemplated that the load transfer connectors 105 may take any shape such as round, oval, square, triangular, or the like. Likewise, while the optional embodiments illustrated in FIGS. 1-8 show two load transfer connectors 105 per reinforcing bar 100, 101, any quantity of one or more load transfer connectors 105 may be included. Likewise, the placement along the reinforcing bar 100, 101 could take any pattern or form. For example, in the optional embodiments illustrated in FIGS. 1-8, the load transfer connectors 105 are aligned along the long axis of the reinforcing bars 100, 101. However, this should be interpreted as merely illustrative, since it is contemplated that the load transfer connectors 105 could be placed in any location and with any pattern.

The load transfer connectors 105 illustrated in FIGS. 1-8 are attached to the reinforcing bars 100, 101. In the optional embodiments of FIGS. 1-5, the load transfer connectors 105 are attached to the surface of the reinforcing bars 100, 101. In the optional embodiment of FIGS. 6-8, the load transfer connectors 105 fit into openings 106 in a reinforcing bar 100. As discussed in greater detail below, the load transfer connectors 105 transfer loads between adjoining reinforcing bars 100, 101 of the reinforcing system. Thus, in the optional embodiments of FIGS. 1-8, the load transfer connectors 105 are located proximate to one end (FIGS. 4-8) or both ends (FIGS. 1-3) of each reinforcing bar 100, 101. However, it is contemplated that the load transfer connectors 105 could, in alternate optional embodiments, be additionally, or alternatively disposed along the surface of the reinforcing bars 100, 101 away from the ends of the reinforcing bars 100, 101. Again, it is contemplated that any quantity of load transfer connectors 105, of any shape and distributed in any manner, may be provided on the reinforcing bars 100, 101. In the optional embodiment of FIGS. 1-5, it is contemplated that the load transfer connectors 105 may be attached to the surface of the reinforcing bars 100, 101, such as by welding, or may be integrally formed with the reinforcing bars 100, 101. In the optional embodiment of FIGS. 6-8, it is contemplated that the load transfer connectors 105 may be fitted into openings 106 in each reinforcing bar 100, 101 to be connected.

A link plate 102 overlies the connection between reinforcing bars 100, 101. The link plate 102 includes openings 106 that mate with the load transfer connectors 105. In one optional embodiment, the openings 106 mate with the load transfer connectors 105 with an interference fit (also known as a friction fit or press fit, as those terms are understood in mechanical engineering). Alternatively, the mating connection between the openings 106 and load transfer connectors 105 may be a looser fit, e.g., a transition fit or running fit. The link plate 102 serves to transfer loads between adjoining reinforcing bars 100, 101 through the interface of the openings 106 and the load transfer connectors 105. Under load, the openings 106 of the link plate 102 bear against the load transfer connectors 105 of one or both of the underlying reinforcing bars 100, 101, or vice versa, thereby reinforcing the monopole 200. Specifically, as the monopole 200 is subjected to bending forces or moments, longitudinal tension or compression forces are created in the reinforcing bars 100, 101. These forces are transferred between the reinforcing bars 100, 101 through the load transfer connectors 105 and openings 106 of the link plate 102 that connect to the load transfer connectors 105.

Figure 2:
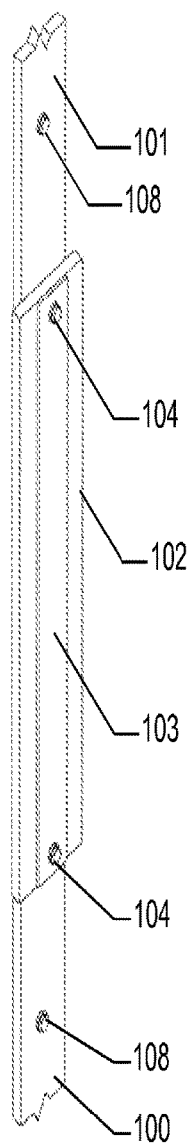
FIG. 2 is an elevated perspective view of an assembled link-plate according to an embodiment of the present invention.
Figure 3:
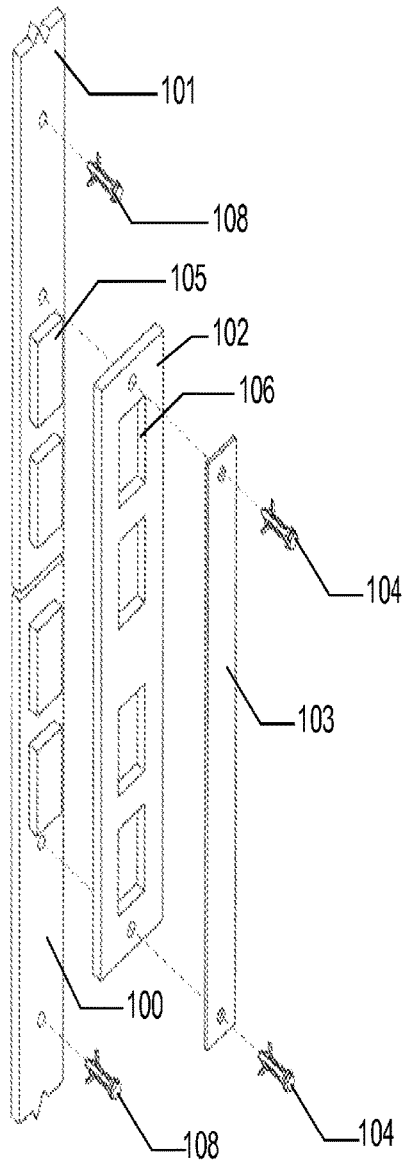
FIG. 3 is an elevated perspective assembly view of a link-plate according to an embodiment of the present invention.

In the optional embodiment of FIGS. 1-3, the link plate 102 may include openings 106 that mate with load transfer connectors 105 on both reinforcing bars to be connected 100, 101. In another optional embodiment illustrated in FIGS. 4-8, the link plate 102 may be welded to (or otherwise attached to fastened to, or formed with) one reinforcing bar 100 with openings 106 to mate with load transfer connectors 105 on the other reinforcing bar 101 to be connected. As may be appreciated, the link plate 102 of such an optional embodiment may be attached (e.g., welded, fastened, or the like) to the reinforcing bar 100 in the shop prior to installation, in the field during installation, or any other time.

In an optional embodiment illustrated in FIGS. 1-5, a cover plate 103 overlies the link plate 102 that connects adjoining reinforcing bars 100, 101 to one another. In one such optional embodiment, the cover plate 103 may be held to the link plate 102 with fasteners 104, such as a Type HB Hollo-Bolt™ or other types of fasteners and such bolts were not intended to resist any of the longitudinal tension or compression forces but merely to secure the assembly together.

Figure 4:
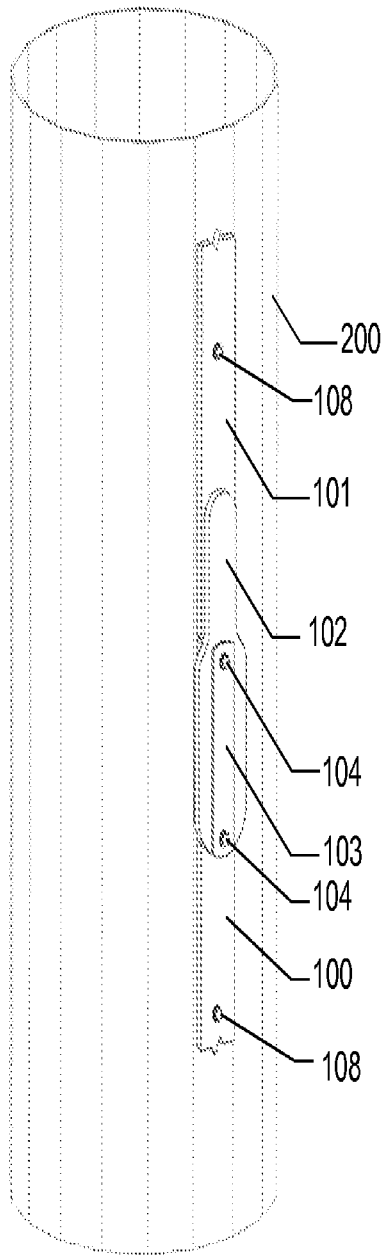
FIG. 4 is an elevated perspective view of a pole and assembled link-plate according to an embodiment of the present invention.
Figure 5:
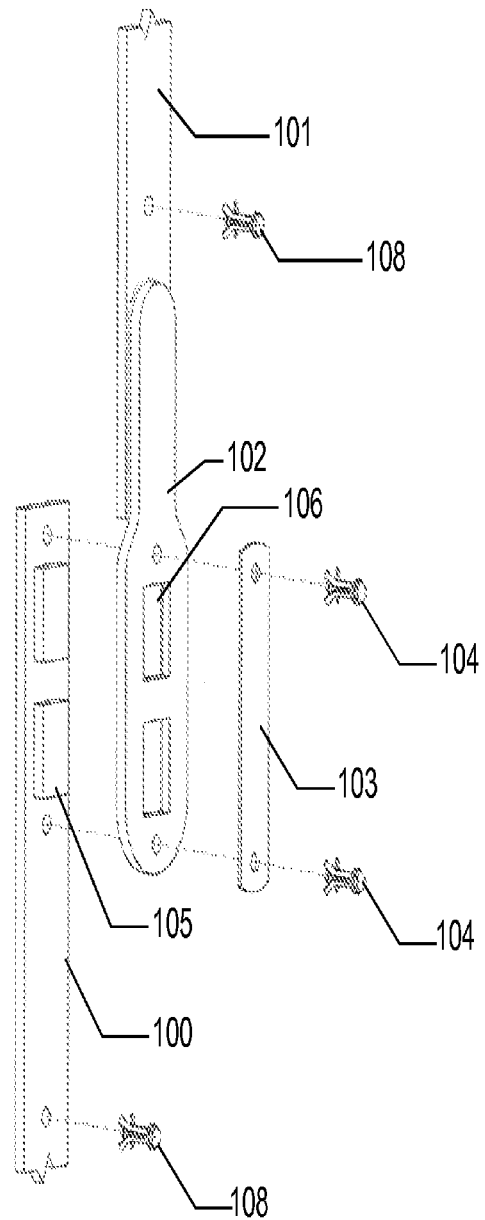
FIG. 5 is an elevated perspective assembly view of a link-plate according to an embodiment of the present invention.
Figure 6:
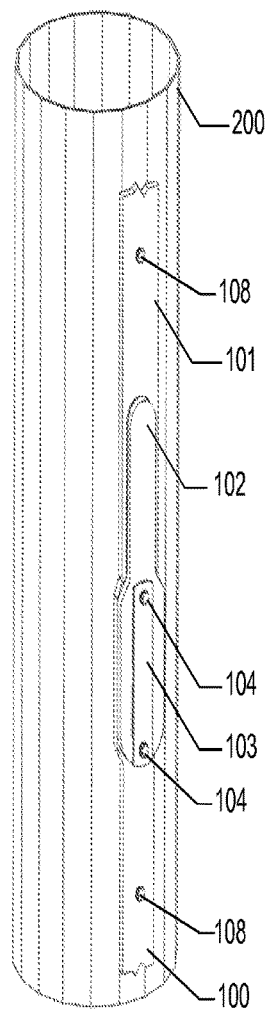
FIG. 6 is an elevated perspective view of a pole and assembled link-plate according to an embodiment of the present invention.
Figure 7:
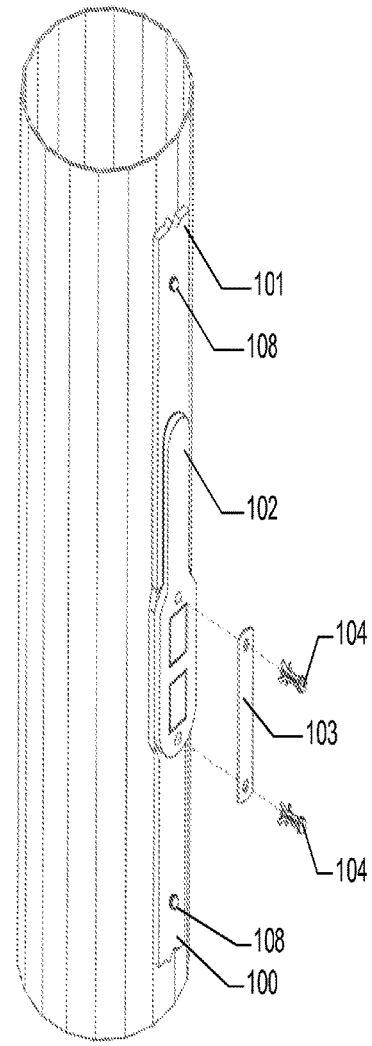
FIG. 7 is an elevated perspective view of a pole and assembled link-plate according to an embodiment of the present invention.
Figure 8:
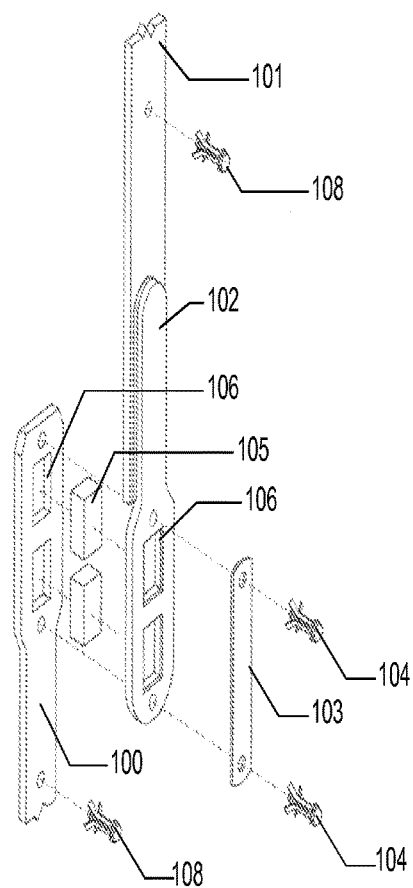
FIG. 8 is an elevated perspective assembly view of a link-plate according to an embodiment of the present invention.

In use, reinforcing bars 100, 101 may be secured to a monopole 200 using bolts or other fasteners 108 that pass through the reinforcing bar 100, 101 and into the monopole 200. Adjoining reinforcing bars 100, 101 may be secured to one another by positioning a link plate 102 over the adjoining reinforcing bars 100, 101, with the openings 106 in the link plate 102 aligned with the load transfer connectors 105 of the underlying reinforcing bars 100, 101. The link plate 102 is secured to the reinforcing bars 100, 101 with the openings 106 mated to the load transfer connectors 105. As illustrated in FIGS. 1-3, the link plate 102 may mate with load transfer connectors 105 on both adjoining reinforcing bars 100, 101 through the openings 106 in the link plate 102. Alternatively, as illustrated in FIGS. 4 and 5, the link plate 102 may be secured to one of the reinforcing bars 100, such as through shop-welding or field-welding the link plate 102 to the reinforcing bar 100, and mated to the load transfer connectors 105 on an adjacent reinforcing bar 101 through the openings 106 in the link plate 102.

Referring generally to FIGS. 1-5, in an optional embodiment, a bolt 104 secures the link plate 102 to one or both of the underlying reinforcing bars 100, 101. In a further optional embodiment, a cover plate 103 may be secured over the link plate 102 to cover the mated openings 106 and load transfer connectors 105. In one such optional embodiment, a fastener 104 secures the cover plate 103, link plate 102, and reinforcing bars 100, 101 together.

Use of the link plate 102 would permit more standardization of parts as only a few link plate designs would be needed to properly splice many sizes and shapes of reinforcing bars 100, 101. Additionally, the link plate 102 could be used on many types of monopole structures, such as wind turbines, pipe poles, stepped poles, tapered poles, or the like. Additionally, using the link plate 102 would be more aesthetic as it would minimize the number of bolts used at the splices. The completed installation would appear more like one continuous reinforcing bar connected to the monopole structure. Thus, the present invention seeks to reduce the amount of drilling needed for splicing the reinforcing plates to thereby speed the installation of monopole reinforcing plates and reduce the cost of augmenting and reinforcing monopoles.

While certain embodiments of the present invention have been shown and described it is to be understood that the present invention is subject to many modifications and changes without departing from the spirit and scope of the claims presented herein.

What is claimed:

1. A system configured to reinforce a monopole, the system comprising:
    a first reinforcing bar having an inner, monopole-engagement surface and an outer surface, the inner and outer surfaces of the first reinforcing bar spaced from one another along a first direction;
    a first generally rectangular load transfer connector disposed on the outer surface of the first reinforcing bar that extends out from the outer surface of the first reinforcing bar;
    a second reinforcing bar having an inner, monopole-engagement surface and an outer surface, the inner and outer surfaces of the second reinforcing bar spaced from one another along the first direction;
    a second generally rectangular load transfer connector disposed on the outer surface of the second reinforcing bar that extends out from the outer surface of the second reinforcing bar; and
    a link plate configured to overlay at least a portion of each of the first reinforcing bar and the second reinforcing bar, the link plate defining first and second openings configured to mate with the first and second load transfer connectors, respectively, when the link plate overlays the at least a portion of each of the first and second reinforcing bars.

2. The system of claim 1, wherein the first and second openings are configured to mate with the first and second load transfer connectors, respectively, when the first and second reinforcing bars are arranged end-to-end.

3. The system of claim 1, wherein each of the first and second reinforcing bars has a first end, and a second end offset from the first end along a second direction, perpendicular to the first direction, and the first and second openings are configured to mate with the first and second load transfer connectors, respectively, when the second end of the first reinforcing bar is disposed adjacent to the first end of the second reinforcing bar.

4. The system of claim 3, wherein the first load transfer connector extends from the first reinforcing bar at a location that is closer to the second end of the first reinforcing bar than the first end of the first reinforcing bar.

5. The system of claim 4, wherein the second load transfer connector extends from the second reinforcing bar at a location that is closer to the first end of the second reinforcing bar than the second end of the second reinforcing bar.

6. The system of claim 4, further comprising a third load transfer connector, wherein the third load transfer connector extends out from the outer surface of the first reinforcing bar at a location that is between the first load transfer connector and the second end of the first reinforcing bar.

7. The system of claim 3, wherein the first reinforcing bar defines at least one aperture configured to receive at least one fastener therethrough and into the monopole so as to secure the first reinforcing bar to the monopole.

8. The system of claim 7, wherein the first load transfer connector extends from the first reinforcing bar at a location that is between the at least one aperture of the first reinforcing bar and the second end of the first reinforcing bar.

9. The system of claim 7, wherein the second reinforcing bar defines at least one aperture configured to receive at least one fastener therethrough and into the monopole so as to secure the second reinforcing bar to the monopole.

10. The system of claim 9, wherein the second load transfer connector extends from the second reinforcing bar at a location that is between the at least one aperture of the second reinforcing bar and the first end of the second reinforcing bar.

11. The system of claim 1, further comprising a cover plate configured to overlay at least a portion of the link plate.

12. The system of claim 1, wherein the first and second openings of the link plate are configured to mate with the first and second load transfer connectors, respectively, with an interference fit.

13. The system of claim 1, wherein the first load transfer connector is formed integrally with the first reinforcing bar.

14. A method for reinforcing a monopole, the method comprising:
    installing a reinforcement system onto the monopole such that first and second reinforcing bars of the reinforcement system are fastened to the monopole, a link plate of the reinforcement system overlies at least a portion of each of the first and second reinforcing bars, a first opening in the link plate mates with a first generally rectangular load transfer connector disposed on the outer surface of the first reinforcing bar that extends from the first reinforcing bar, and a second opening in the link plate mates with a second generally rectangular load transfer connector disposed on the outer surface of the second reinforcing bar that extends from the second reinforcing bar.

15. The method of claim 14, wherein the installing step comprises a step of fastening the first and second reinforcing bars to the monopole.

16. The method of claim 15, wherein the fastening step comprises fastening the first and second reinforcing bars to the monopole such that a second end of the first reinforcing bar is adjacent a first end of the second reinforcing bar, the first load transfer connector is closer to the second end of the first reinforcing bar than a first end of the first reinforcing bar, and the second load transfer connector is closer to the first end of the second reinforcing bar than a second end of the second reinforcing bar.

17. The method of claim 14, wherein the installing step comprises a step of overlaying the link plate over at least a portion of each of the first and second reinforcing bars such that the first opening mates with the first load transfer connector and such that the second opening mates with the second load transfer connector.

18. The method of claim 14, wherein the installing step comprises installing the reinforcement system to the monopole such that a cover plate overlays at least a portion of the first and second openings.

19. The method of claim 14, wherein the installing step comprises overlaying a cover plate over at least a portion of the first and second openings.

* * * * *